(12) United States Patent
Kim et al.

(10) Patent No.: US 11,712,684 B2
(45) Date of Patent: Aug. 1, 2023

(54) SUPPORTED METAL CATALYST AND METHOD OF FORMING THE SAME

(71) Applicant: SEOUL NATIONAL UNIVERSITY R&DB FOUNDATION, Seoul (KR)

(72) Inventors: Do Heui Kim, Seoul (KR); Yonghyun Lim, Seoul (KR); Minyeong Gim, Seoul (KR); Kwan Young Lee, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 17/499,422

(22) Filed: Oct. 12, 2021

(65) Prior Publication Data

US 2022/0118429 A1    Apr. 21, 2022

(30) Foreign Application Priority Data

Oct. 21, 2020  (KR) .................. 10-2020-0136935

(51) Int. Cl.
*B01J 29/40* (2006.01)
*B01J 37/02* (2006.01)
*C07C 2/82* (2006.01)

(52) U.S. Cl.
CPC ......... *B01J 29/405* (2013.01); *B01J 37/0213* (2013.01); *C07C 2/82* (2013.01); *C07C 2523/08* (2013.01); *C07C 2529/40* (2013.01)

(58) Field of Classification Search
CPC ........................ B01J 29/405; B01J 37/0213; B01J 2229/186; B01J 2229/37; B01J 35/002; B01J 23/08; B01J 37/02; B01J 37/08; C07C 2/82; C07C 2523/08; C07C 2529/40

See application file for complete search history.

(56) References Cited

FOREIGN PATENT DOCUMENTS

HU         202213 B    *  7/1987
JP         S64-61462 A    3/1989

OTHER PUBLICATIONS

English Translation of HU 202213B.*
Chi-Ying Hsieh et al., "Ga-Substituted Nanoscale HZSM-5 in Methanol Aromatization: The Cooperative Action of the Brønsted Acid and the Extra-Framework Ga Species," Industrial Engineering Chemistry Research, May 25, 2018.
He Xiao et al., "A highly efficient Ga/ZSM-5 catalyst prepared by formic acid impregnation and in situ treatment for propane aromatization," Catalysis Science & Technology, Jun. 5, 2015.
Reinaldo Monque et al., "Analytical method for the determination of intra- and extraframework gallium species in zeolite catalyst," Zeolites, 1992, pp. 806-809, vol. 12, Issue 7.

* cited by examiner

*Primary Examiner* — Thuan D Dang

(57) ABSTRACT

A supported metal catalyst and a method of forming the same is provided. The supported metal catalyst according to embodiments of the present invention is formed by a method comprising supporting a metal on a support and treating the support supporting the metal with an acid. The method of forming a supported metal catalyst according to embodiments of the present invention comprises supporting a metal on a support and treating the support supporting the metal with an acid.

4 Claims, 4 Drawing Sheets
(4 of 4 Drawing Sheet(s) Filed in Color)

SUPPORTED METAL CATALYST AND METHOD OF FORMING THE SAME

BACKGROUND OF THE INVENTION

1. Field of the Invention

The present invention relates to a supported metal catalyst and a method of forming the same.

2. Description of the Related Art

Currently, industrially produced BTX is mostly produced from crude oil through the naphtha reforming process. As shale gas development has been actively carried out in North America over the past decade, the supply of light hydrocarbons is increasing. Being able to produce BTX from light hydrocarbons can reduce the dependence of BTX production on crude oil and make efficient use of the explosively growing gas supply. However, the aromatization catalyst currently used to produce BTX from C3/C4 gas has a problem with low activity.

SUMMARY OF THE INVENTION

In order to solve the above mentioned problems, the present invention provides a supported metal catalyst having good catalytic activity.

The present invention provides a method of forming the supported metal catalyst.

The other objects of the present invention will be clearly understood with reference to the following detailed description and the accompanying drawings.

A supported metal catalyst according to embodiments of the present invention is formed by a method comprising supporting a metal on a support and treating the support supporting the metal with an acid.

The metal may comprise gallium. The support may comprise a zeolite. The acid may comprise a hydrochloric acid.

The supported metal catalyst may be an aromatization catalyst.

A method of forming a supported metal catalyst according to embodiments of the present invention comprises supporting a metal on a support and treating the support supporting the metal with an acid.

The metal may comprise gallium. The support may comprise a zeolite. The acid may comprise a hydrochloric acid.

The activity of the supported metal catalyst may be controlled by the amount of the supported metal and the concentration of the acid.

A portion of the metal supported by the support may be removed by the acid treatment.

The acid treatment increases the dispersion degree of the metal in the support.

The supported metal catalyst according to embodiments of the present invention may have good catalytic activity. In addition, the supported metal catalyst can be formed by a simple process. The supported metal catalyst may be, for example, a gallium zeolite catalyst in which gallium is supported on zeolite. The gallium zeolite catalyst may have good aromatization reaction activity, and may be effectively used not only for propane aromatization, but also for olefin aromatization, ethane aromatization, etc. requiring high dispersion degree of gallium.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will be more clearly understood from the following detailed description taken in conjunction with the accompanying drawings, in which.

DESCRIPTION OF SPECIFIC EMBODIMENTS

Hereinafter, a detailed description will be given of the present invention with reference to the following embodiments. The purposes, features, and advantages of the present invention will be easily understood through the following embodiments. The present invention is not limited to such embodiments, but may be modified in other forms. The embodiments to be described below are nothing but the ones provided to bring the disclosure of the present invention to perfection and assist those skilled in the art to completely understand the present invention. Therefore, the following embodiments are not to be construed as limiting the present invention.

A supported metal catalyst according to embodiments of the present invention is formed by a method comprising supporting a metal on a support and treating the support supporting the metal with an acid.

The metal may comprise gallium (Ga). The support may comprise a zeolite. The acid may comprise a hydrochloric acid (HCl).

The supported metal catalyst may be used as an aromatization catalyst because the supported metal catalyst has a good aromatization activity.

A method of forming a supported metal catalyst according to embodiments of the present invention comprises supporting a metal on a support and treating the support supporting the metal with an acid.

The metal may comprise gallium (Ga). The support may comprise a zeolite. The acid may comprise a hydrochloric acid (HCl).

The activity of the supported metal catalyst may be controlled by the amount of the supported metal and the concentration of the acid. A portion of the metal supported by the support may be removed by the acid treatment. The acid treatment increases the dispersion degree of the metal in the support.

In order to precisely control the activity of the supported metal catalyst, the removal amount of the supported metal, the dispersion degree of the supported metal, and the like, the concentration of the acid used for the acid treatment is preferably low. For example, the acid treatment may be performed using dilute hydrochloric acid. In addition, since a portion of the supported metal is removed by the acid treatment, the metal is preferably supported in an excess amount greater than the final target supported amount of the supported metal catalyst.

Figure 1:
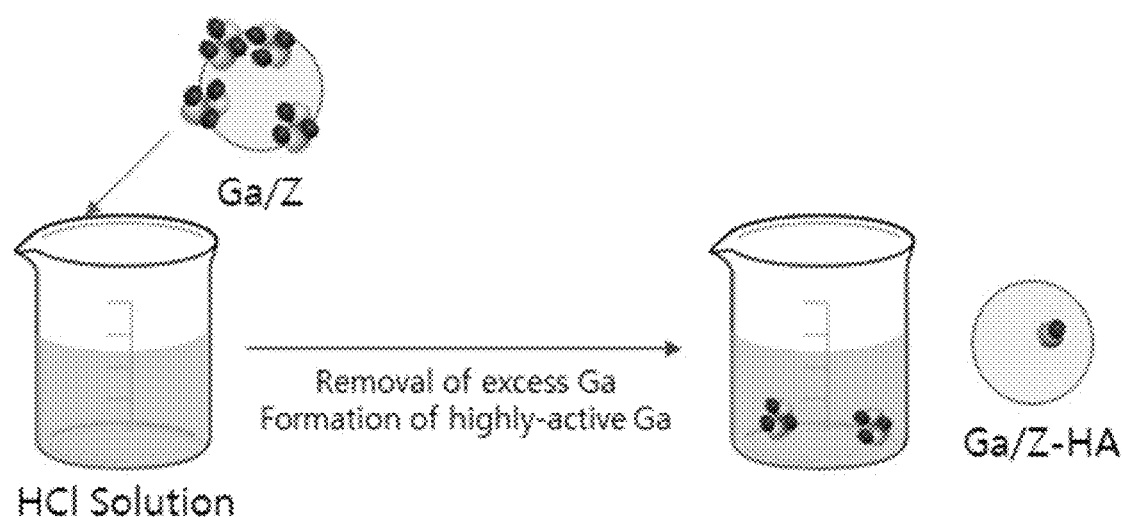
FIG. 1 shows a method of forming a supported metal catalyst according to one embodiment of the present invention.

Embodiment—Formation Example of Gallium Zeolite Catalyst (Ga/Z-HA) Subjected to Acid Treatment FIG. 1 shows a method of forming a supported metal catalyst according to one embodiment of the present invention.

Referring to FIG. 1, a catalyst was formed in which gallium was supported in excess on HZSM-5 zeolite by an impregnation method prior to acid treatment. A precursor solution was prepared by dissolving 0.54 g of gallium nitrate hydrate in 10 ml of distilled water so that the content of gallium in the catalyst was about 7 wt %. HZSM-5 zeolite having a Si:$Al_2$ ratio of 23:1 was added to the precursor solution, and heated to 85° C. while stirring at a stirring speed of 300 RPM. After all of the water evaporated, the remaining catalyst was dried in an oven at 105° C. for more than 10 hours, and then calcined at 550° C. for hours to form a zeolite catalyst with excess gallium supported. The catalyst thus formed was named Ga/Z.

3.2 ml of a 36% hydrochloric acid aqueous solution was added to 157 ml of distilled water to prepare a hydrochloric acid aqueous solution having a concentration of about 0.2M. After 0.8 g of Ga/Z was added to the hydrochloric acid aqueous solution, the mixture was stirred at a high temperature of 160° C. at a stirring speed of 300 RPM for 3 hours. Thereafter, the solution was filtered through a filter paper, washed with about 2 L of distilled water, dried in an oven at 105° C. for more than hours, and then calcined at 550° C. for 5 hours. The gallium zeolite catalyst subjected to the acid treatment was named Ga/Z-HA (HA is an abbreviation for hydrochloric acid).

Comparative Example 1—Formation Example of Gallium Zeolite Catalyst (Ga/Z-IMP) by an Impregnation Method A catalyst was formed in which gallium was supported in a small amount on HZSM-5 zeolite by a general impregnation method. A precursor solution was prepared by dissolving 0.022 g of gallium nitrate hydrate in 10 ml of distilled water. The amount of gallium nitrate was used so that the gallium content in the catalyst was the same as the Ga/Z-HA catalyst. HZSM-5 zeolite having a Si:$Al_2$ ratio of 23:1 was added to the precursor solution, and heated to 85° C. while stirring at a stirring speed of 300 RPM. After all of the water evaporated, the remaining catalyst was dried in an oven at 105° C. for more than 10 hours, and then calcined at 550° C. for 5 hours. The zeolite catalyst in which a small amount of gallium was supported was formed. The catalyst thus formed was named Ga/Z-IMP (IMP stands for impregnation).

Comparative Example 2—Formation Example of a Catalyst (Ga/(Z-HA)-IMP) in which Gallium was Supported on the HZSM-5 Zeolite Treated with Acid Only HZSM-5 zeolite was treated with acid and then a small amount of gallium was supported on the HZSM-5 treated with the acid to form a catalyst. 3.2 ml of a 36% hydrochloric acid aqueous solution was added to 157 ml of distilled water to prepare a hydrochloric acid aqueous solution having a concentration of about 0.2M. HZSM-5 zeolite having a Si:$Al_2$ ratio of 23:1 was added to the hydrochloric acid aqueous solution, and stirred at a high temperature of 160° C. at a stirring speed of 300 RPM for 3 hours. Thereafter, the solution was filtered through a filter paper, washed with about 2 L of distilled water, dried in an oven at 105° C. for more than 10 hours, and then calcined at 550° C. for 5 hours.

A method of supporting gallium on HZSM-5 zeolite subjected to acid treatment is the same as in comparative example 1. A precursor solution was prepared by dissolving 0.022 g of gallium nitrate hydrate in 10 ml of distilled water. The acid-treated HZSM-5 zeolite was added to the precursor solution and heated to 85° C. while stirring at a stirring speed of 300 RPM. After all of the water evaporated, the remaining catalyst was dried in an oven at 105° C. for more than 10 hours, and then calcined at 550° C. for 5 hours to form a catalyst supporting gallium on the acid-treated HZSM-5 zeolite. The catalyst thus formed was named Ga/(Z-HA)-IMP ((Z-HA) means that the zeolite was first acid-treated).

Comparative Example 3—Formation Example of Gallium Zeolite Catalyst (HA-IE) by Ion Exchange Method A catalyst was formed in which gallium was ion-exchanged with HZSM-5 under acidic conditions. In the process of acid treatment of Ga/Z, a large amount of gallium is dissolved into an acid solution, which is similar to the ion exchange process, so this comparative example was included as a control for Ga/Z-Ha. 3.2 ml of a 36% hydrochloric acid aqueous solution was added to 157 ml of distilled water to prepare an hydrochloric acid aqueous solution having a concentration of about 0.2M. After 0.54 g of gallium nitrate hydrate was dissolved in the hydrochloric acid aqueous solution, HZSM-5 zeolite having a Si:$Al_2$ ratio of 23:1 was added. The solution was stirred at a high temperature of 160° C. at a stirring speed of 300 RPM for 3 hours, filtered through filter paper, washed with about 2 L of distilled water, dried in an oven at 105° C. for more than 10 hours, and then calcined at 550° C. for 5 hours. The gallium zeolite catalyst ion-exchanged under acid conditions was named HA-IE (IE is an abbreviation of ion-exchange).

[Production of BTX by Propane Aromatization Using the Gallium Zeolite Catalysts According to the Embodiment of the Present Invention and the Comparative Examples 1 to 3]

A propane aromatization reactions were performed at a reaction temperature of 550° C. using the gallium zeolite catalysts according to the embodiment and the comparative examples. The gas composition used was nitrogen:propane=2:1, and the total gas hourly space velocity (GHSV) was 3600 ml/$g_{catalyst}$/h. After charging 0.2 g of the catalyst in a quartz fixed bed reactor, the temperature was raised at a rate of 10° C./min to the reaction temperature under a nitrogen atmosphere. After the temperature reached 550° C., propane gas was flowed to perform an aromatization reaction. Conversion rate of propane and yield were calculated by equations 1, 2, and 3, respectively.

Conversion rate(%)=(number of moles of reacted reactant×number of carbons)÷(number of moles of supplied reactant×number of carbons)×100  [Equation 1]

Selectivity(%)=(number of moles of product×number of carbons)÷(number of moles of reacted reactant×number of carbons)×100  [Equation 2]

Yield(%)=Conversion rate×Selectivity÷100  [Equation 3]

Figure 2:
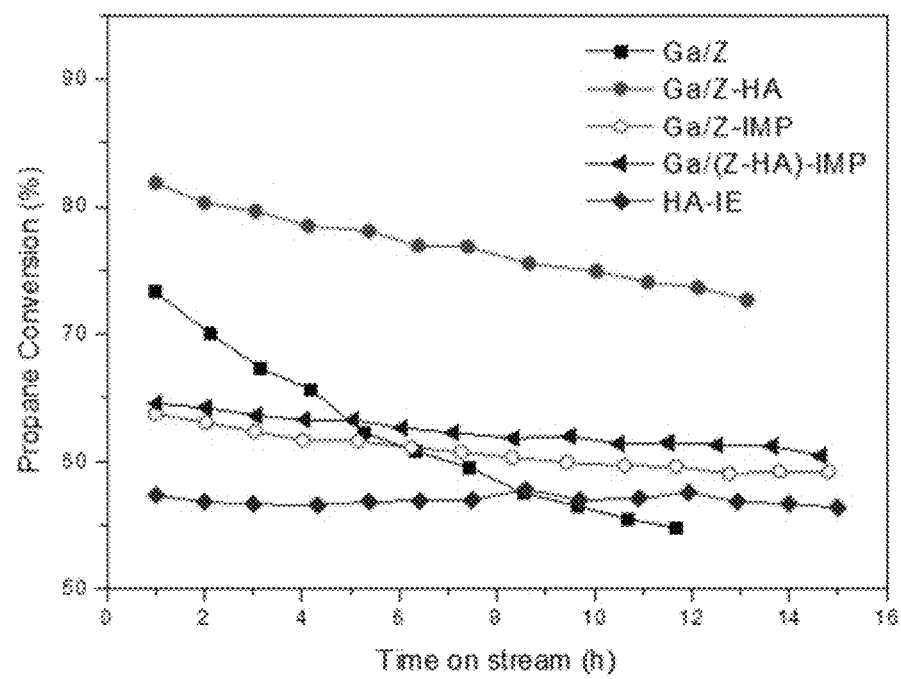
FIGS. 2 and 3 show the propane aromatization reaction activity of gallium zeolite catalysts according to the embodiment of the present invention and the comparative examples.
Figure 3:
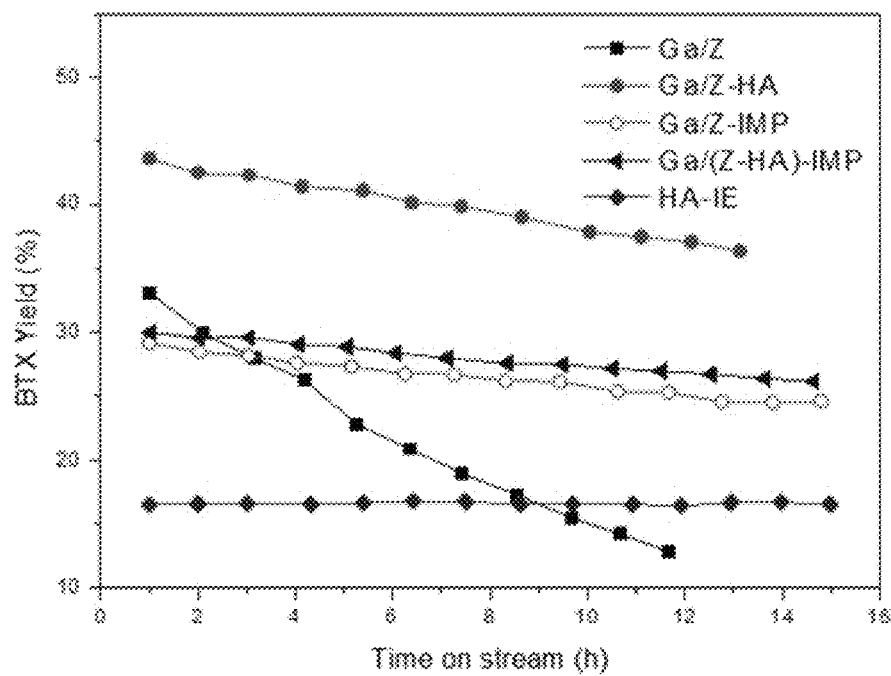

FIGS. 2 and 3 show the propane aromatization reaction activity of gallium zeolite catalysts according to the embodiment of the present invention and the comparative examples. FIG. 2 shows conversion rate of propane and FIG. 3 shows BTX yield.

Referring to FIGS. 2 and 3, Ga/Z loaded with excess gallium exhibits rapid deactivation over the reaction time because the excess gallium blocks the pores of the zeolite, inhibit mass transfer in the catalyst and promote coke formation. Ga/Z-HA showed an initial BTX yield that was about 2.6 times higher than that of HA-IE and about 1.5 times higher than those of Ga/Z-IMP and Ga/(Z-HA)-IMP. That is, the gallium zeolite catalyst formed by acid treatment according to the embodiment of the present invention exhibited better propane aromatization reaction activity than the gallium zeolite catalyst formed according to the comparative examples to have a similar gallium content. Ga/Z-IMP and Ga/(Z-HA)-IMP did not show a significant difference in reaction activity, indicating that supporting gallium after acid treatment of HZSM-5 zeolite has no effect. Therefore, the high activity of Ga/Z-HA is due to the change of gallium rather than the change by the acid treatment of the support.

Analysis Example—Characterization and Comparison of the Gallium Zeolite Catalysts According to the Embodiment of the Present Invention and Comparative Examples 1 to 3

Figure 4:
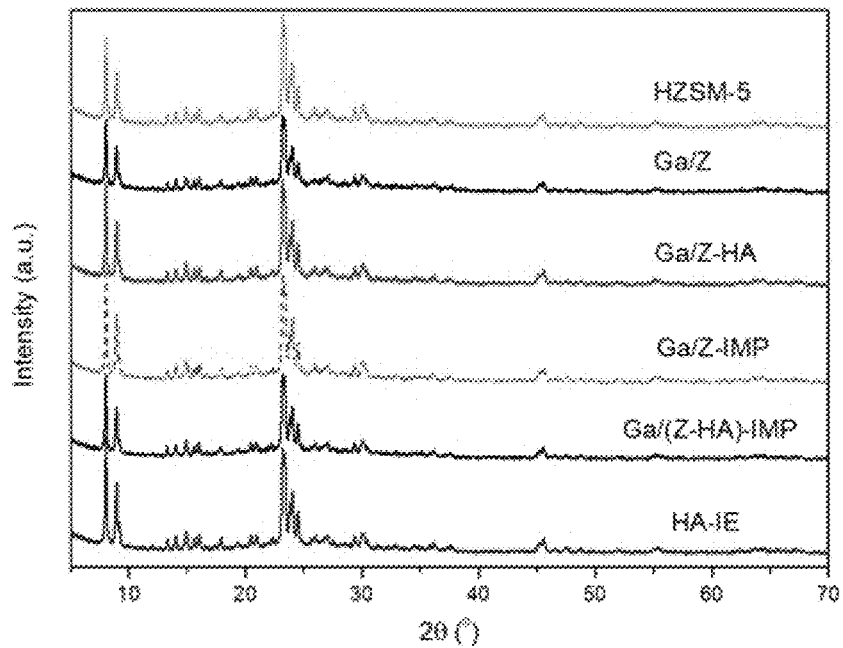
FIG. 4 shows the analysis results of the characteristics of gallium zeolite catalysts according to the embodiment of the present invention and the comparative examples.

FIG. 4 and Table 1 show the analysis results of the characteristics of gallium zeolite catalysts according to the embodiment of the present invention and the comparative examples.

Referring to FIG. 4 and Table 1, Ga/Z-HA contains 0.34 wt % of gallium compared to Ga/Z having 6.8 wt % of gallium, and most of the gallium present in Ga/Z is removed by acid treatment according to the embodiment of the present invention. Ga/Z-IMP and Ga/(Z-HA)-IMP were successfully formed with gallium content similar to Ga/Z-HA, and HA-IE contained almost no gallium. That is, it can be seen that ion exchange hardly occurs under acidic conditions, and gallium species exhibiting high aromatization activity are produced only through the process of first supporting gallium in excess and then removing a portion of the gallium by acid treatment as in the embodiment.

In addition, the crystallinity of Ga/Z-IMP, Ga/(Z-HA)-IMP, and HA-IE was not significantly different from that of HZSM-5, whereas Ga/Z-HA showed relatively low crystallinity. It seems that the crystallinity of the particles was inhibited in the process of removing a portion of the gallium by the acid treatment. The surface area and pore volume of the catalyst calculated from the BET analysis did not show a significant difference in any of the four catalysts of the embodiment of the present invention and comparative examples.

TABLE 1

| Catalyst | Ga loading (wt %)[a] | Relative Crystallinity (%)[b] | $S_{BET}$ (m²/g) | Pore volume (cm³/g) | |
|---|---|---|---|---|---|
| | | | | Micropore[c] | Mesapore (2~50 nm)[d] |
| Ga/Z | 6.80 | 59.8 | 272 | 0.118 | 0.066 |
| Ga/Z-HA | 0.34 | 82.8 | 333 | 0.158 | 0.080 |
| Ga/Z-IMP | 0.34 | 95.5 | 323 | 0.155 | 0.070 |
| Ga/(Z-HA)-IMP | 0.36 | 92.6 | 337 | 0.161 | 0.079 |
| HA-IE | 0.04 | 94.8 | 331 | 0.159 | 0.071 |

Figure 5:
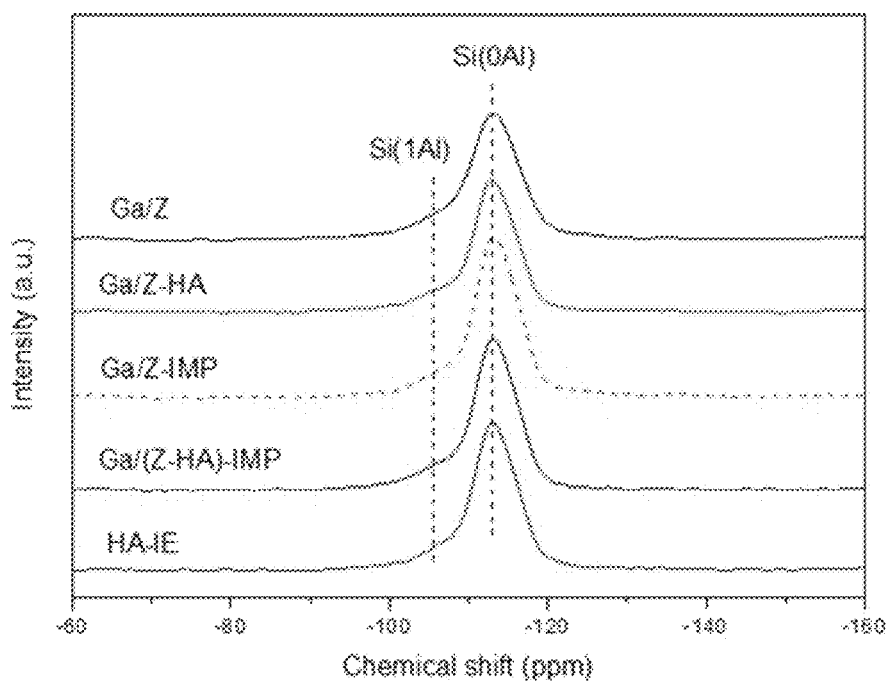
FIGS. 5 and 6 show $^{27}$Al-NMR and $^{29}$Si-NMR analysis results for gallium zeolite catalysts according to the embodiment of the present invention and the comparative examples.
Figure 6:
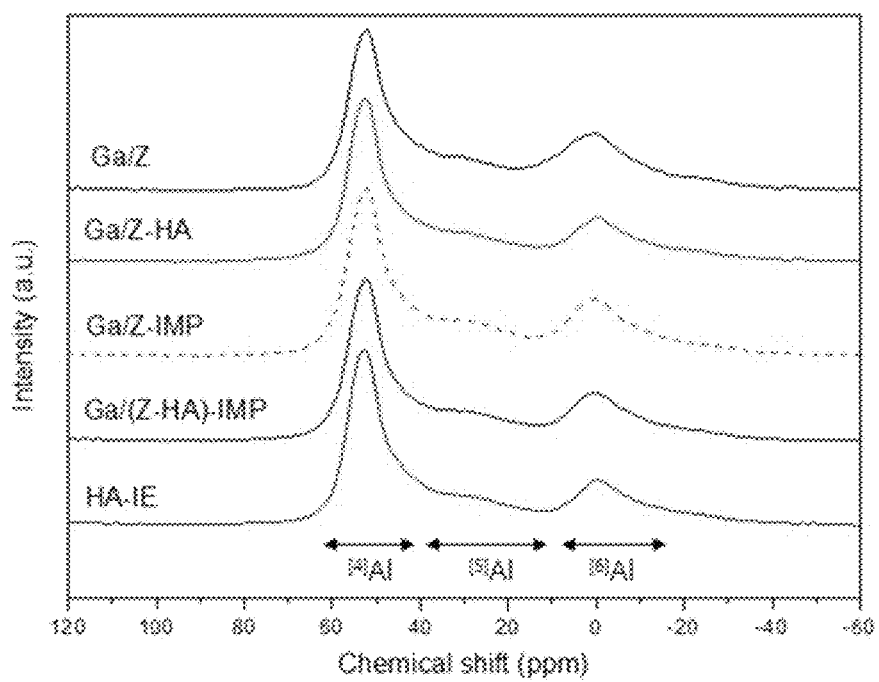

[a]Determined by ICP-AES analysis
[b]Calculated by XRD, referenced to HZSM-5 (Z)
[c]Estimated by t-plot method
[d]BJH(Barret-Joyner-Hallender) desorption pore volume in the range of 2~50 nm FIGS. 5 and 6, and Table 2 show $^{27}$Al-NMR and $^{29}$Si-NMR analysis results for gallium zeolite catalysts according to the embodiment of the present invention and the comparative examples.

Referring to FIGS. 5 and 6, and Table 2, in the case of Si/Al ratio, Ga/Z, Ga/Z-IMP, Ga/(Z-HA)-IMP, and HA-IE were all similar, but the value increased in the case of Ga/Z-HA. This means that a portion of aluminum constituting the zeolite lattice structure is also removed in the process of removing the excess gallium by the acid treatment, and it is also related to the decrease in the crystallinity of Ga/Z-HA shown in Table 1. The ratio of aluminum constituting the lattice structure to the aluminum outside the lattice ($Al_{FW}/Al_{EFW}$) is high in the catalysts (Ga/Z-HA, Ga/(Z-HA)-IMP, HA-IE) that contain acid treatment in the forming process, which means that the aluminum outside the lattice is effectively removed by the acid treatment.

TABLE 2

| Catalyst | Si/Al[a] | $Al_{FW}/Al_{EFW}$[b] | Brønsted acid site (μmol/g)[c] | Lewis acid site (μmol/g)[c] | Brønsted/Lewis acid site ratio (B/L) |
|---|---|---|---|---|---|
| Ga/Z | 24.1 | 1.90 | 230 | 274 | 0.84 |
| Ga/Z-HA | 27.8 | 2.47 | 230 | 198 | 1.17 |
| Ga/Z-IMP | 25.2 | 2.08 | 316 | 144 | 2.20 |
| Ga/(Z-HA)-IMP | 24.1 | 2.40 | 291 | 149 | 1.96 |
| HA-IE | 25.5 | 2.52 | 305 | 160 | 1.91 |

Figure 7:
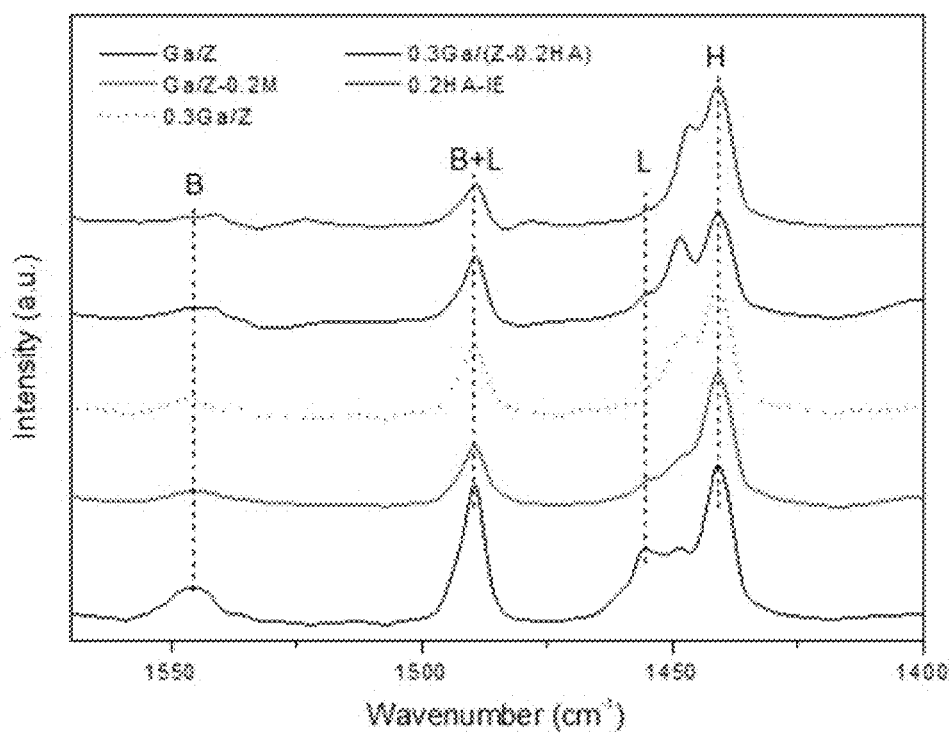
FIG. 7 shows the analysis results of the acid characteristics of gallium zeolite catalysts according to the embodiment of the present invention and the comparative examples using pyridine adsorption FT-IR analysis and ammonia TPD analysis.

[a]Determined by $^{29}$Si-NMR
[b]Determined by $^{27}$Al-NMR
[c]Calculated by NH3-TPD, FT-IR spectra of adsorbed pyridine FIG. 7 and Table 2 show the analysis results of the acid characteristics of gallium zeolite catalysts according to the embodiment of the present invention and the comparative examples using pyridine adsorption FT-IR analysis and ammonia TPD analysis.

Referring to FIG. 7 and Table 2, few B acid sites and many L acid sites of Ga/Z are due to gallium contained in excess to block the pores of the zeolite. The L acid sites of Ga/Z-HA significantly reduced compared to Ga/Z because a lot of gallium was removed, and since the B acid sites were recovered and lost by aluminum removal from the lattice, the amount of the B acid sites was similar. Ga/Z-HA has more L-acid sites compared to Ga/Z-IMP and Ga/(Z-HA)-IMP of the same gallium content because gallium, which serves as an L-acid site, is effectively dispersed and acts as an efficient acid site.

Figure 8:
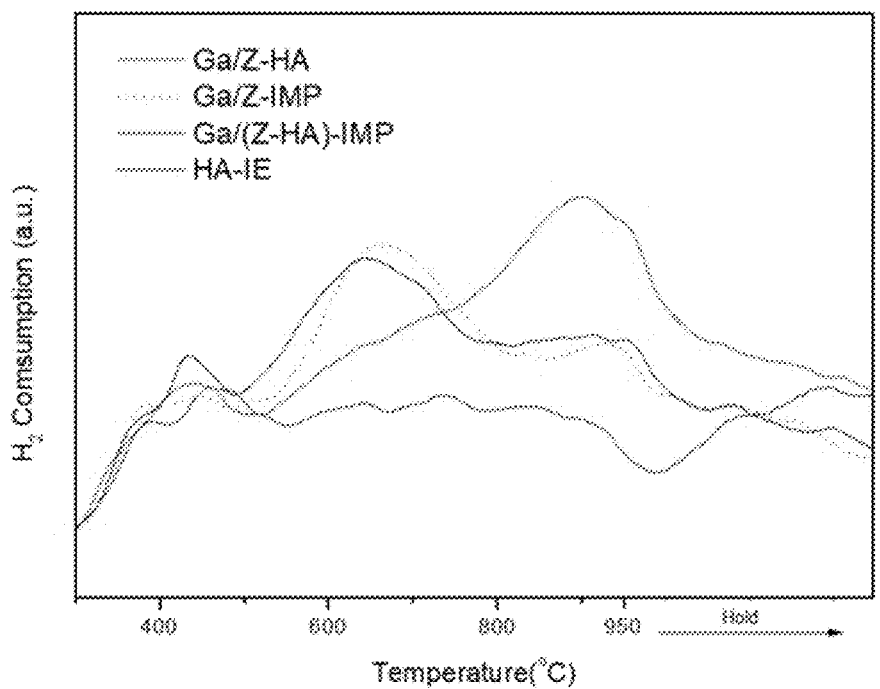
FIG. 8 shows the analysis results of the form of gallium present in gallium zeolite catalysts according to the embodiment of the present invention and the comparative examples using $H_2$-TPR analysis.

FIG. 8 shows the analysis results of the form of gallium present in gallium zeolite catalysts according to the embodiment of the present invention and the comparative examples using $H_2$-TPR analysis.

Referring to FIG. 8, Ga/Z-IMP and Ga/(Z-HA)-IMP show the reduction peak of gallium at about 650° C., and their positions are very similar. The peak at this temperature is known as the reduction peak of gallium oxide ($Ga_2O_3$), and since the peak positions of the two catalysts are similar, regardless of whether the support is treated with an acid or not, in the gallium zeolite catalyst formed by the impregnation method, gallium mainly exists as gallium oxide. The gallium reduction peak of Ga/Z-HA appears at a higher temperature of about 940° C. This is known as a reduction peak of gallium oxide in a well-dispersed form in zeolite or $GaO^+$ ion-exchanged with zeolite. That is, Ga/Z-HA exists in a form in which gallium remaining in the catalyst after Ga/Z acid treatment is well dispersed, and has a different form from gallium formed by the impregnation method. This is in good agreement with the lower B/L ratio of Ga/Z-HA compared to Ga/Z-IMP and Ga/(Z-HA)-IMP, whereby Ga/Z-HA can have good propane aromatization activity. HA-IE did not show a distinct peak, an this means that ion exchange of gallium hardly occurred in acidic conditions, and is the same as the low gallium content of HA-IE in Table 1.

As mentioned above, both gallium and zeolite present in the gallium zeolite catalyst are affected by acid treatment. In the case of zeolite, aluminum outside the lattice is effectively removed, and aluminum constituting the lattice structure is not significantly affected. However; in the case of the Ga/Z-HA catalyst, aluminum in the lattice structure is partially removed, which is considered to be the removal of the aluminum in the lattice while the gallium is removed. Since various physical and chemical properties of Ga/Z-IMP and Ga/(Z-HA)-IMP are similar and there is no significant difference in propane aromatization activity, the acid treatment of the support does not significantly affect the reaction activity. The Ga/Z-HA catalyst is different from other catalysts in the form of gallium, and gallium is well dispersed in the zeolite phase by the acid treatment, so that it can have good propane aromatization reaction activity.

As above, the exemplary embodiments of the present invention have been described. Those skilled in the art will appreciate that the present invention may be embodied in other specific ways without changing the technical spirit or essential features thereof. Therefore, the embodiments disclosed herein are not restrictive but are illustrative. The scope of the present invention is given by the claims, rather than the specification, and also contains all modifications within the meaning and range equivalent to the claims.

What is claimed is:

1. A method of forming a supported metal catalyst comprising:
    loading gallium on a zeolite in an amount greater than a final supported amount; and
    treating the zeolite supporting the loaded gallium with hydrochloric acid,
    wherein a portion of the gallium supported by the zeolite is removed by the hydrochloric acid treatment, and
    wherein an amount of the gallium removed by the hydrochloric acid treatment is greater than the final amount of the remaining portion of the gallium supported by the zeolite after the hydrochloric acid treatment.

2. The method of claim 1, wherein the activity of the supported metal catalyst is controlled by the amount of the supported gallium and the concentration of the hydrochloric acid.

3. The method of claim 1, wherein the activity of the supported metal catalyst is controlled by the amount of the supported gallium and the concentration of the hydrochloric acid.

4. The method of claim 1, wherein the remaining portion of the gallium supported by the zeolite after the hydrochloric acid treatment is extra-framework gallium.

* * * * *